United States Patent [19]

Solomon

[11] Patent Number: 5,626,559
[45] Date of Patent: May 6, 1997

[54] OPHTHALMIC DEVICE FOR DRAINING EXCESS INTRAOCULAR FLUID

[75] Inventor: Arie Solomon, Givatayim, Israel

[73] Assignee: Ramot University Authority for Applied Research and Industrial Development Ltd., Tel Aviv, Israel

[21] Appl. No.: 431,530

[22] Filed: May 1, 1995

[30] Foreign Application Priority Data

May 2, 1994 [IL] Israel ......................................... 109499

[51] Int. Cl.$^6$ ............................ A61M 5/00; A61M 35/00
[52] U.S. Cl. ................................................. 604/9; 604/289
[58] Field of Search ............................. 604/8, 9, 10, 294, 604/295

[56] References Cited

U.S. PATENT DOCUMENTS

| | | | |
|---|---|---|---|
| 3,788,327 | 1/1974 | Donowitz et al. | 604/9 |
| 4,402,681 | 9/1983 | Haas et al. | 604/9 |
| 4,457,757 | 7/1984 | Molteno . | |
| 4,968,296 | 11/1990 | Ritch et al. . | |
| 5,127,901 | 7/1992 | Odrich | 604/9 |

FOREIGN PATENT DOCUMENTS

| | | |
|---|---|---|
| 1671295A1 | 8/1991 | U.S.S.R. . |
| 1718913A | 3/1992 | U.S.S.R. . |

Primary Examiner—Robert A. Clarke
Assistant Examiner—David J. Cho
Attorney, Agent, or Firm—Wigman, Cohen, Leitner & Myers, P.C.

[57] ABSTRACT

An ophthalmic device for removal of excess intraocular fluid from the eye, the device having a general shape resembling that of a thumbtack and comprising a head portion, and a leg portion essentially normal to the head portion. The head portion is dome-shaped with its edges defining an essentially planar surface which together with the dome-shaped portion defines a captured space. The leg portion has one end attached to or integral with the head portion within the captured space, and has another, free end, provided with an annular shoulder tapered in the direction of the free end. The leg defining a duct leading from one or more first opening at the free end to one or more second openings at the proximal end, with the one or more second openings leading into the captured space, the duct being provided with one-way valve means permitting flow of fluid only in the direction of the first openings to the second openings. The distance between the surface and the shoulder is about that of the thickness of the cornea or sclera of the eye. The device being fixed in the eye by inserting the free end of the leg through the cornea or sclera, following which the shoulder engages the inner surface of the cornea or sclera and the edges of the head portion rest on the external surface of the cornea of sclera.

5 Claims, 2 Drawing Sheets

OPHTHALMIC DEVICE FOR DRAINING EXCESS INTRAOCULAR FLUID

FIELD OF THE INVENTION

The present invention provides a device for the drainage of excess intraocular fluid. The device of the invention is useful for the treatment of a variety of pathologies associated with development of pressure within the eye, e.g. for the treatment of glaucoma.

BACKGROUND OF THE INVENTION

Glaucoma, is a common name for a variety of disorders in which the pressure of the intraocular fluid in the eye is elevated which results eventually in the destruction of the optic nerve. Glaucoma is one of the leading causes of blindness in the world.

Treatment of glaucoma is either by means of medication or surgery. The simplest form of surgery involves the opening of a passage in the cornea or sclera which allows drainage of humoral fluid from the eye to the exterior, e.g. into the sub-conjunctival space. More advanced surgical procedures involves draining of humoral fluid from the eye by means of a device which provides a controlled passage for outflow of humoral fluid from the intraocular space. Devices for draining humoral fluid from the eye and means for their use have been described in Soviet Patents 1671295 and 1718913 and U.S. Pat. Nos. 4,457,757 and 4,968,296.

It is the object of the present invention to provide a relatively small implantable device useful for removal of excess humoral fluid to the extraocular space, which is relatively small and provides relatively little inconvenience to the patient.

GENERAL DESCRIPTION OF THE INVENTION

The present invention provides an ophthalmic device for draining of excess intraocular fluid from the eye, the device having a general shape resembling that of a thumbtack and comprising a head portion, and a leg portion essentially normal to said head portion; the head portion being dome-shaped, the edges thereof defining an essentially planar surface which together with the dome-shaped portion defines a captured space; the leg portion having one end thereof attached to or integral with said head portion within said captured space, and having another, free end, provided with an annular shoulder tapered in the direction of said free end, said leg defining a duct leading from one or more first openings at said free end to one or more second opening at said proximal end, said one or more second opening leading into said captured space, the duct being provided with one-way way valve means permitting flow of fluid only in the directly of said first opening to said second openings; the distance between said surface and said shoulder is about that of the thickness of the cornea or sclera of the eye; the device being fixed in the eye by inserting said free end of said leg through the cornea or sclera, following which said shoulder engages the inner surface of the cornea or sclera and the edges of said head portion rest on the external surface of the cornea of sclera.

The device preferably comprises also discharge openings in said head portion allowing discharge or fluid accumulating in said captured space.

The device is typically implanted under the conjunctiva whereby the intraocular fluid is drained into the sub-conjunctiva space.

The invention will now be illustrated by a description of a nonlimiting specific embodiment with occasional reference to the annexed drawings.

DESCRIPTION OF SPECIFIC EMBODIMENTS

Figure 1:
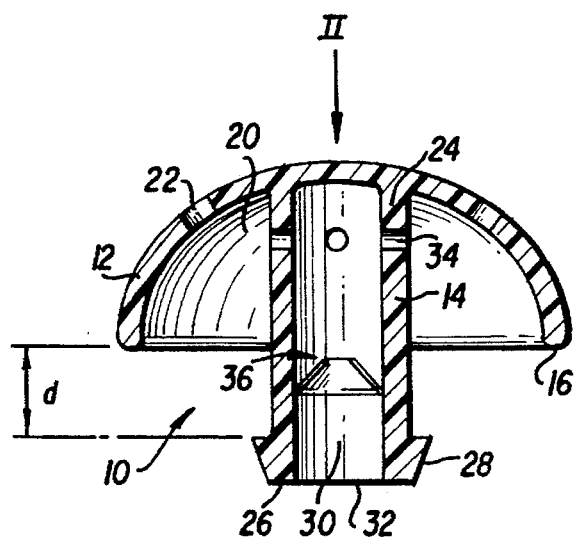
FIG. 1 shows a longitudinal cross-section through a device of the invention wherein the head portion and the leg portion are integral with one another.
Figure 2:
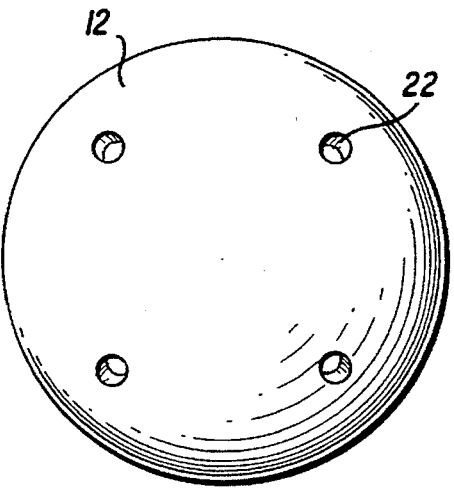
FIG. 2 is a view of the device of FIG. 1 from the direction of arrow II in FIG. 1.

Reference is first being made to FIGS. 1 and 2 showing a device in accordance with one embodiment of the invention. The device may be made of a variety of inert materials such as silicone, polymethyl methacrylate, PYREX™ brand borosilicate glass, TEFLON™ brand polytetrafluoroethylene.

Figure 5:
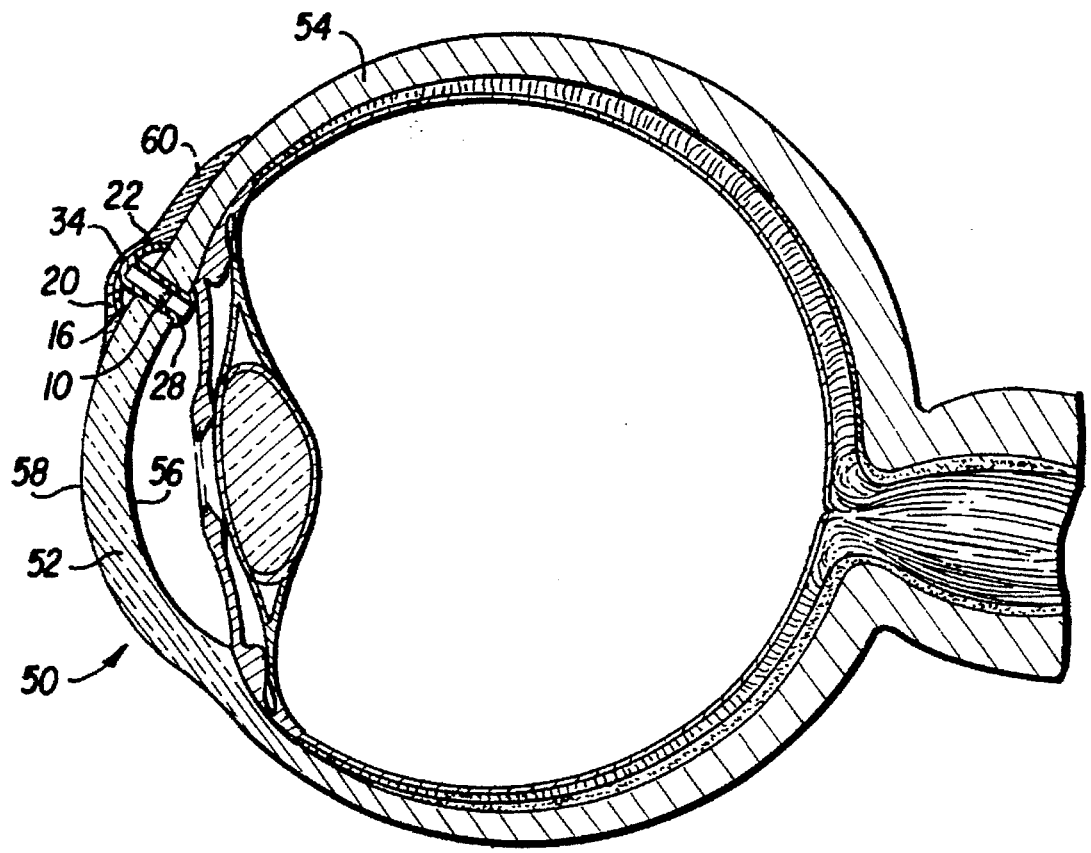
FIG. 5 shows a cross-sectional view of the eye with the device of the invention in situ.

The device generally designated 10 has a shape resembling that of a thumb tack and comprises an essentially circular dome-shaped head portion 12 having a concave inner surface 13 and an apex 15 and a leg portion 14 essentially normal to the head portion. The edge 16 of the head portion defines a planar surface 18 which together with the dome-shaped head portion defines a captured space 20. As can be seen in FIG. 5, the radius of curvature of the head portion 12 is less than the radius of curvature of the eye, whose surface acts as the planar surface 18 when the device 10 is in situ. This results in the formation of the captured fluid receiving space 20 having an annular opening 21 between the inner surface of the head portion 12 and the eye. The curvature of the head portion is preferably such that it encompasses within capture space 20 about half of the length of the leg portion. The head portion 12 comprises a plurality of discharge openings 22, four in this specific embodiment, close to the edge of the dome for the release of fluid which accumulates in the captured space.

The leg portion 14 has one end 24 which is integral with the head portion and has a free end 26 provided with an annular shoulder 28 which is tapering in the direction of the free end. The distance D between surface 18 and shoulder 28 should be about equal to the thickness of the cornea or sclera of the eye to which the device is intended.

The leg portion 14 defines a duct 30 leading from an opening 32 at free end 26 to a plurality of openings 34 adjacent end 24, which open into captured space 20. It will be appreciated that rather than a single opening 32, the device can also have a plurality of openings at end 26 similar to openings 34 at end 24.

Duct 30 is provided with a one-way valve 36, which is typically a flapper-type or spring-type valve which opens when the pressure of fluid exceeds a certain predetermined pressure. The valve allows a flow of fluid only in the direction of from opening 32 to openings 34.

Figure 3:
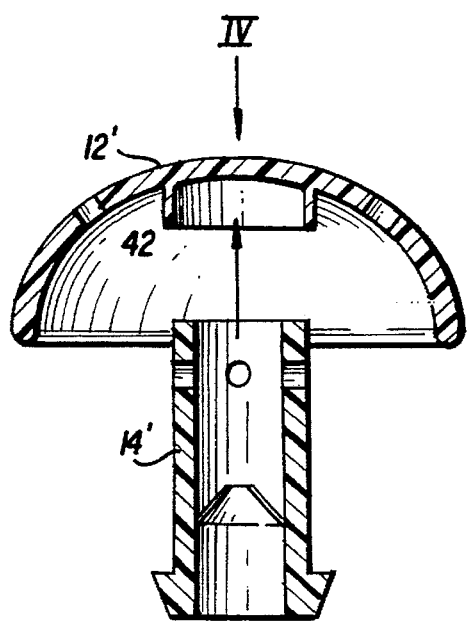
FIG. 3 shows a longitudinal cross-sectional view of a device where the head portion and the leg portion are separate members which are being attached to one another.
Figure 4:
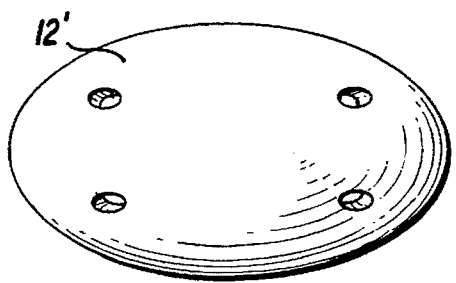
FIG. 4 shows a view of the device of FIG. 3 from the direction of arrow IV in FIG. 3.

Reference is now being made to FIGS. 3 and 4 showing another embodiment of a device in accordance with the invention. The differences between this device and that shown in FIGS. 1 and 2 are in that the head portion 12' and the leg portion 14' are two separate members which are attached to one another by means of annular socket 42 in head portion 12'; and further in that rather than circular, the dome-shaped head portion 12'

Figure 6:
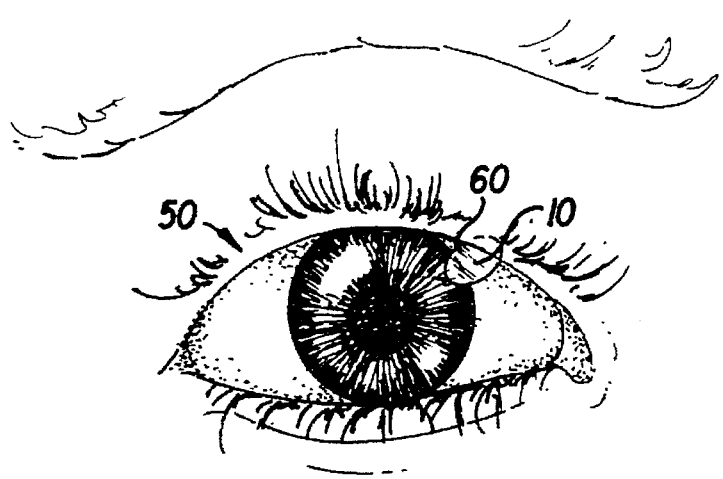
FIG. 6 shows a front view of the eye of FIG. 5.

Reference is now being made to FIGS. 5 and 6 showing a device 10 in situ in eye 50. The device is typically inserted at the border line between the cornea 52 and the sclera 54 close to the linked margin of the cornea. The device is typically positioned at the upper-right or upper-left portion of the eye. For implantation of the device the conjunctiva is opened, fornix base and then a small hole or tunnel is created by a needle smaller than the diameter of the device's leg. The leg of the device is then inserted through the hole. Upon insertion, shoulders 28 come into engagement with the inner surface 56 of the cornea of sclera and the edges 16 of the head portion come to rest on the external surface 58. The conjunctiva is then closed at the end of the procedure. When the intraocular pressure increases, valve 36 opens and fluid flows into captured space 20 through openings 34. From captured space 20 fluid can exit through discharge openings 22 into the sub-conjunctiva space creating a bleb of fluid 60.

As known, eyes in different individuals differ in their physical parameters, particularly in the thickness of the cornea or sclera. Accordingly, the physical dimensions of the device will be different for use in different eyes, particularly a difference in the distances D (see FIG. 1). The devices may typically be provided in several standard sizes. Typical dimensions of the device for human eyes are as follows:
diameter of head portion (of a circular shape: 3 to 4 mm;
diameter of leg portion: 0.75 to 1.0 mm;
distance D: 1 to 1.5 mm;

Although a certain embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

I claim:

1. An implant device for draining intraocular fluid from the anterior cavity of an eye comprising:

a generally domed shaped head portion having a concave inner surface and at least one opening for draining fluid, said head portion terminating in a circular or elliptical edge adapted to engage the eye so as to define a fluid receiving space bounded by said head portion and said eye;

a leg portion comprising a first end adapted to pierce the sclera or cornea of the eye, an opposite second end mounted to the concave inner surface of said head portion, a first fluid opening at said first end, a second fluid opening at said second end in communication with said fluid receiving space, and a fluid duct communicating said first and second fluid openings;

wherein an opening is defined between said edge and said leg portion for absorption of said fluid by the area of the eye between said edge and said leg; and a valve for controlling fluid flow through said implant.

2. The eye implant device of claim 1 wherein said head portion has a radius of curvature less than the radius of curvature of the eye.

3. The implant device of claim 1, wherein said generally domed shaped head portion is releasably secured to said leg portion.

4. An implant device for draining intraocular fluid from the interior chamber of an eye comprising:

a generally domed shaped head portion having a concave inner surface and at least one opening for draining fluid, said head portion terminating in a circular or elliptical edge adapted to engage the eye so as to define a fluid receiving space bounded by said head portion and said eye;

a leg portion comprising a first end adapted to pierce the sclera or cornea of the eye, an opposite second end mounted to the concave inner surface of said head portion, a first fluid opening at said first end, a second fluid opening at said second end in communication with said fluid receiving space, and a fluid duct communicating said first and second fluid openings; and a valve for controlling fluid flow through said implant; wherein said leg portion includes a plurality of spaced second openings communicating with said fluid receiving space.

5. An implant device for draining intraocular fluid from the interior chamber of an eye comprising:

a generally domed shaped head portion having a concave inner surface and at least one opening for draining fluid, said head portion terminating in a circular or elliptical edge adapted to engage the eye so as to define a fluid receiving space bounded by said head portion and said eye;

a leg portion comprising a first end adapted to pierce the sclera or cornea of the eye, an opposite second end mounted to the concave inner surface of said head portion, a first fluid opening at said first end, a second fluid opening at said second end in communication with said fluid receiving space, and a fluid duct communicating said first and second fluid openings; and a valve for controlling fluid flow through said implant; wherein said generally domed shaped head portion has an apex, and wherein said head portion has at least one fluid drainage opening disposed closer to said apex than said edge.

* * * * *